US009182218B2

(12) United States Patent
Campagne et al.

(10) Patent No.: US 9,182,218 B2
(45) Date of Patent: Nov. 10, 2015

(54) METHOD AND DEVICE FOR NONDESTRUCTIVE TESTING OF MATERIAL HEALTH ESPECIALLY IN THE FILLETS OF A COMPOSITE PART

(71) Applicant: Airbus Operations (S.A.S.), Toulouse (FR)

(72) Inventors: Benjamin Campagne, Saint Herblain (FR); Patrick Passelande, Coueron (FR); Franck Bentouhami, Chavannes en Paillers (FR)

(73) Assignee: AIRBUS OPERATIONS (S.A.S.), Toulouse (FR)

( * ) Notice: Subject to any disclaimer, the term of this patent is extended or adjusted under 35 U.S.C. 154(b) by 0 days.

(21) Appl. No.: 14/491,586

(22) Filed: Sep. 19, 2014

(65) Prior Publication Data

US 2015/0070708 A1    Mar. 12, 2015

Related U.S. Application Data

(63) Continuation of application No. PCT/EP2013/055464, filed on Mar. 15, 2013.

(30) Foreign Application Priority Data

Mar. 20, 2012    (FR) .................................. 12 52494

(51) Int. Cl.
*G01B 11/06*    (2006.01)
*G01B 9/02*    (2006.01)
(Continued)

(52) U.S. Cl.
CPC ............ *G01B 11/06* (2013.01); *G01B 9/02091* (2013.01); *G01B 11/02* (2013.01);
(Continued)

(58) Field of Classification Search
CPC ............... G01B 11/06; G01B 9/02091; G01B 11/0675; G01B 11/02; G01N 21/4795; G01N 21/8422; G01N 2021/1787; G01N 2021/8438; G01N 2021/8472
See application file for complete search history.

(56) References Cited

U.S. PATENT DOCUMENTS 5,125,740 A *  6/1992  Sato et al. ..................... 356/128
6,172,752 B1 * 1/2001  Haruna et al. ................ 356/503
(Continued)

FOREIGN PATENT DOCUMENTS

JP    2010/052255 A    3/2010

OTHER PUBLICATIONS

Benjamin Campagne, Hubert Voillaume, Patrick Passelande, GaetanMarion, "Optical Coherence Tomography for Inspection of Aeronautic Composite Parts," 13th International Symposium on Nondestructive Characterization of Materials (NDCM-XIII), May 20-24, 2013, Le Mans, France.*
International Search Report for Application No. PCT/EP2013/055464 datde Apr. 15, 2013.

*Primary Examiner* — Michael A Lyons
*Assistant Examiner* — Violeta A Prieto
(74) *Attorney, Agent, or Firm* — Jenkins, Wilson, Taylor & Hunt, P.A.

(57) ABSTRACT

The disclosure relates to devices for the completely automated detection and characterization of a resin flash in a part consisting of a composite material, the device including an OCT measuring head including an OCT measuring module, a manipulator capable of moving the OCT head in space, a control for the manipulator, and a computer including a memory for acquiring the definition of the geometry of the area to be tested, for recording the measurements, for storing a criterion file, and for performing calculations pertaining to the comparison of the recording with the criterion file. The disclosure also relates to a method for detection and characterization of such a resin flash.

6 Claims, 3 Drawing Sheets

(51) Int. Cl.
*G01N 21/84* (2006.01)
*G01B 11/02* (2006.01)
*G01N 21/47* (2006.01)

(52) U.S. Cl.
CPC ........ *G01N21/4795* (2013.01); *G01N 21/8422* (2013.01); *G01N 2021/8438* (2013.01); *G01N 2021/8472* (2013.01)

(56) References Cited

U.S. PATENT DOCUMENTS

| | | | |
|---|---|---|---|
| 2004/0239951 A1* | 12/2004 | Yamanishi et al. | 356/614 |
| 2008/0252899 A1* | 10/2008 | Morosawa et al. | 356/479 |
| 2009/0168074 A1* | 7/2009 | Monchalin et al. | 356/502 |
| 2010/0007894 A1 | 1/2010 | Suehira | |
| 2010/0312524 A1* | 12/2010 | Siercks et al. | 703/1 |

* cited by examiner

METHOD AND DEVICE FOR NONDESTRUCTIVE TESTING OF MATERIAL HEALTH ESPECIALLY IN THE FILLETS OF A COMPOSITE PART

CROSS-REFERENCE TO RELATED APPLICATIONS

This application is a continuation of PCT Patent Application No. PCT/EP2013/055464 filed Mar. 15, 2013 which claims the benefit of and priority to French Patent Application No. FR 12 52494, filed Mar. 20, 2012, the entire disclosures of which are incorporated by reference herein.

TECHNICAL FIELD

This disclosure relates to a method and device for nondestructive testing of material health especially in the fillets of a composite part. The disclosure more particularly, but not exclusively, relates to automatic nondestructive testing of a large part formed from a composite material comprising continuous fibrous reinforcements in a resin. Furthermore, the device and the method of the disclosure are particularly useful in the field of composite parts that form structural assemblies or subassemblies of an aircraft.

BACKGROUND

The constituent elements of the structure of a vehicle, and of an aircraft in particular, must be tested to check that flaws that are inherent to the process of their manufacture, and that would be liable, in particular, to decrease the structural withstand properties of these parts in service, are absent therefrom. The size of these flaws is, generally, several orders of magnitude smaller than the size of the parts thus tested. More particularly, in the case of composite parts comprising a resin reinforced by a fibrous reinforcement taking the form of continuous fibers, these parts form integral subassemblies of the structure, which are unitarily formed by molding, and which may have complex shapes.

In the prior art, it is known to test this type of part with techniques that use the propagation of ultrasound through the thickness of the part to detect therein cracks, delamination, resin deficiencies, etc. These ultrasonic testing techniques advantageously use one or more laser beams, which are focused on the surface of the part and moved over this surface by a robot or a manipulator, to create an excitation and to obtain an interferometric measurement. These nondestructive testing techniques allow automatic "dry" testing of the entirety of the volume of the part to be performed, no acoustic coupling agent being used between the sensors and the surface on which the testing is carried out.

However, in the case of a part formed from a composite material reinforced by long or continuous fibers, flaws that are liable to have an influence on the mechanical properties of the part, but the presence of which is not detected by ultrasonic testing, or which require, in order to be detected by such testing, operating conditions that are not compatible with industrial conditions, or indeed the detection and above all characterization of which requires destructive testing, exist. Thus, flaws such as pleating or corrugation of the fibers can only be detected in micrographic sections or by nonautomatable visual methods such as the detection of an orangey "flash" when the tested zone of the part is illuminated with a white light. The visual method referred to as the "resin flash" method takes advantage of the fact that fiber pleats or corrugations create bodies of resin, mainly on the surface, in the zones in which these pleats are observed, i.e. zones in which the fibers must follow tortuous paths and in which the course of the path does not allow a tension to be applied to the fibers, such as in the concave zones of the fillet radii between two faces. These bodies of resin are detected by illuminating the surface, the light of this illumination being modified by the translucent resin that, in the absence of local reinforcement, generates a bright spot. This detection technique is as old as the use of composites comprising fibrous reinforcements in an organic matrix, to the point that the flaw and its detection technique are not often differentiated, both commonly being designated by the term "resin flash".

Now, analysis of micrographic sections only provides local information that is not representative of the extent, and therefore the severity, of the flaw, and the flash method does not enable quantitative characterization of the flaw, the latter method in addition being highly subjective and depending on the experience of the operator implementing it.

SUMMARY

This disclosure aims to solve the drawbacks of the prior art and provides, for this purpose, a method for automatically detecting and characterizing a resin flash on the surface of a composite part comprising a matrix formed from a transparent or scattering resin and a fibrous reinforcement, the method comprising:

a) obtaining a geometric definition of the zone of the part to be tested;

b) obtaining a file, referred to as the criteria file, comprising resin thickness distribution tolerances corresponding to the nature of the zone to be tested;

c) illuminating a portion, referred to as the measurement point, of the surface of the zone to be tested using a laser source having a low temporal coherence;

d) measuring the resin thickness at the measuring point using an optical coherence tomography approach;

e) recording the thickness value measured in step d) and the spatial coordinates of the measurement point;

f) moving the laser source to another measurement point and repeating steps c) to f) until the entire test zone has been covered; and g) comparing the resin thickness variation profile of the zone to be tested with the criteria file.

Thus, because it uses an Optical Coherence Tomography (OCT) measurement technique, the method of the disclosure makes it possible to obtain the topography of resin thickness, down to the first ply (114) in the measurement zone in question, and to obtain this topography automatically when the OCT measurement head is borne by a manipulator that is configured to move the head over the surface of the part. By comparing this topography to pre-recorded criteria, the part may be declared in or out of specification, again automatically. These tolerance criteria may be determined, for example experimentally, by carrying out steps c) to f) of the method of the disclosure on samples containing known flaws.

The disclosure also relates to a fully automatic device for implementing the method of the disclosure, which device comprises:

i) a measurement head comprising an OCT module;

ii) a manipulator configured to move the OCT head in space; the and iii) an information-processor comprising a controller configured to pilot the manipulator and a computer with memory for acquiring the definition of the geometry of the zone to be tested, for recording the measurements, for storing the criteria file and for carrying out calculations relating to the comparison of the recording with the criteria file.

Thus, the use of such a device allows the testing of a part with respect to resin flash to be fully automated.

This disclosure may be implemented according to the advantageous embodiments described below, which may be considered individually or in any technically workable combination.

Advantageously, the method of the disclosure comprises, before step g), a step comprising:

h) calculating the slope of the resin thickness variation in one of the scan directions.

Thus, the method of the disclosure allows, by way of a parameter that is simple to measure, the "signature" of a superficial resin flash to be automatically detected.

According to one embodiment of the method of the disclosure, the method comprises carrying out steps c) to g) with a measurement head comprising a first module and, if the presence of a resin flash is detected in step g), the method comprises:

j) changing the OCT measurement head;

k) carrying out steps c) to g) with the new measurement head comprising an OCT measurement module configured to improve the detection precision of the resin flash.

Thus, the presence of a resin flash being characterized by the presence of thickness anomalies extending over quite large distances, a first scan allows a rapid first detection level to be obtained, then a second scan, carried out over the same test zone or over another zone, makes a more precise detection and measurement possible, the combination of these steps increasing the rapidity with which the part can be tested.

Advantageously, the device of the disclosure comprises:

v) an optical path, called the measurement leg, of length LM, comprising a scanning mirror configured to project onto the surface of the part the laser radiation from the low temporal coherence source; and vi) an optical path, called the reference leg, separate from the optical path of the measurement leg, and comprising an optical fiber of length Lf and a reference mirror placed at a distance Lz from the exit of the optical fiber such that LM=Lf+Lz.

According to this embodiment, a device of the disclosure allows the OCT measurement principle to be implemented at a relatively large distance from the part while retaining a compact measurement head the operating principle of which enables laser ultrasonic shots to be produced by another source. Thus, the device of the disclosure allows various measurement types to be combined in a single placement of the part to be tested.

According to one embodiment, a device of the disclosure comprises:

vii) structure for changing the active OCT measurement head; and viii) a second OCT measurement head configured to adjust the focal distance of the low coherence laser beam relative to the surface of the part.

Thus, a device of the disclosure is configured to implement the measurement method described above comprising two measurement phases with different precision levels.

BRIEF DESCRIPTION OF DRAWINGS

Nonlimiting embodiments of the disclosure herein are described below with reference to FIGS. 1 to 7, in which.

DETAILED DESCRIPTION

Figure 1:
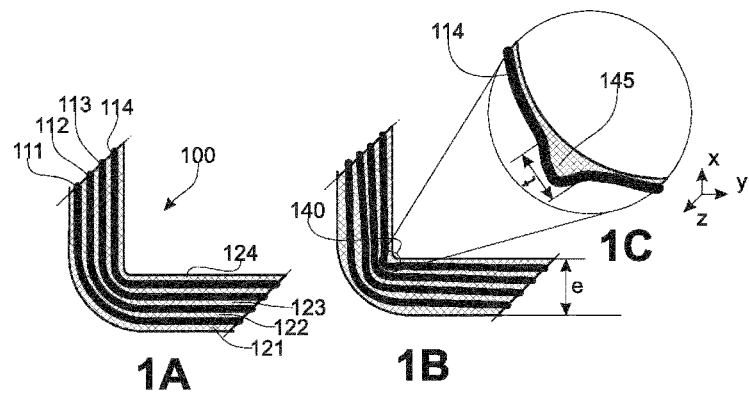
FIG. 1 illustrates a cross-sectional view of a fillet radius of a stratified composite part, FIG. 1A in the absence of a pleat type flaw, FIG. 1B according to an example in which a pleat is present, and FIG. 1C a detail view of the resin thickness down to the first ply in the presence of a flaw.

As shown in FIG. 1A, a composite part (100) is formed from a stratification of plies (111, 112, 113, 114) of fibrous reinforcements that are separated by resin layers (121, 122, 123, 124) of substantially uniform thickness. By way of nonlimiting example, the plies may be formed from unidirectional wovens or unidirectional webs or of multidirectional nonwovens of continuous carbon, glass or aramide fibers. The resin layers may be thermosetting (epoxy resin), or thermoplastic. This stratification is obtained by any method known in the art, from dry or prepreg plies. As shown on FIG. 1B, in specific zones of the stratification where it is difficult to apply a tension to the fibers during deposition, corrugations or pleats (140) may appear. The presence of such pleats, or corrugations, locally decreases the reinforcing capacity of the fibers and may also lead to zones of deformation or stress concentration. Such pleats (140) extend over a number of plies. As the overall thickness (e) of the part is set by the tool used to bake or consolidate the composite, the presence of these corrugations is not detected by a simple thickness measurement and the stratification structure is not enough modified to detect the presence of such corrugations by acoustic techniques. In contrast, as shown on FIG. 1C, the presence of this pleat results in a localized variation (145) in the thickness of resin between the external face of the part and the first ply (114) and which forms a heap of resin. This heap of resin, commonly called resin flash (145), is of small transverse extent (t in the xy plane) but of clearly much greater (several orders of magnitude) longitudinal extent (along z). Thus, if t is about one millimeter, the longitudinal extent of the resin flash (145) is frequently several hundred millimeters, even several meters. Thus, in accordance with the present disclosure it is established that the height and shape of the resin flash (145) are representative of the fiber pleats and corrugations located behind this resin flash (145), in the thickness of the part, and that measuring the thickness of the resin, and especially determining the resin thickness variation, down to the first ply (114) allows the characteristic signature of a resin flash resulting from a fiber pleat or corrugation to be detected, and thus that this information may advantageously be used to quantify this type of defect.

Figure 2:
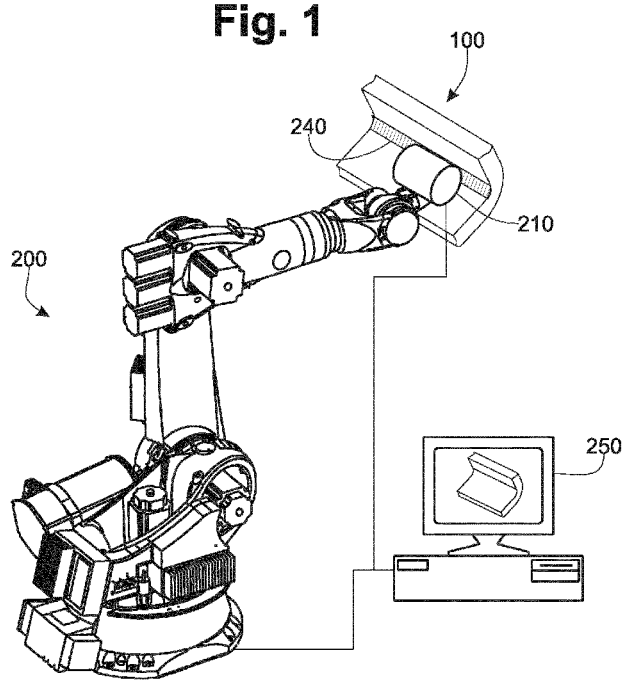
FIG. 2 schematically illustrates a perspective view of the device of the disclosure.

As shown in FIG. 2, the device of the disclosure herein comprises a manipulator (200) configured to move an OCT measurement head (210) along the part (100) at a substantially constant distance from the surface of the part, the distance being compatible with the focal distance of the low temporal coherence laser source of the OCT device. For this purpose, the manipulator (200) is preferably controlled by an information-processor device (250) comprising a recorded geometric definition (715) of the part (100) to be tested and a spatial position of the part (100) in the reference frame of the manipulator (200). Advantageously, the information-processor (250) also controls the measurement head (210) and carries out the acquisition of the measuring points along the zone (240) to be tested, thereby allowing these measurement points to be located with precision on the recorded geometric definition (715) of the part (100) to be tested. Preferably, this acquisition is carried out in the zones that are most likely to be subject to fiber pleating, for example in the fillets connecting two non-coplanar faces, and preferably in the concave portion of these fillets.

Figure 3:
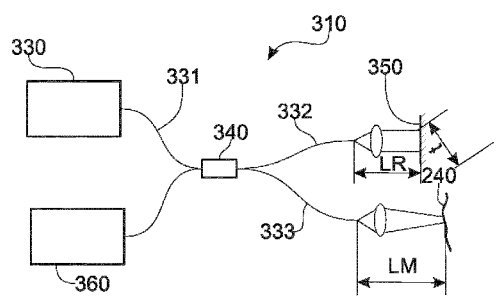
FIG. 3 is a schematic view of an OCT measurement module.

Referring for example to FIG. 3, the OCT measurement method uses a low temporal coherence light source (330). The illuminating beam is focused on the surface of the zone to be tested. Photons backscattered by the part interfere with a reference beam, the reference beam being obtained by splitting a primary beam (331) of the light source in a beam splitter (340), one half (333) of the primary beam (331) is directed toward the surface (240) of the zone to be tested, thereby forming a measurement leg, of length LM, and the other half (332) of the primary beam (331) is directed toward a reference mirror (350), forming a reference leg of length LR. The length of the measurement leg and the length of the reference leg are equal. With a spectrometer detector (360) a signal quantifying the interference of the beams (331, 332, 333) is generated and properties of the part, especially its thickness are therefrom deduced. The measure of the thickness using the OCT approach is possible only in transparent or translucent media. Thus, this thickness measurement allows only a measurement of the local thickness of the resin layer (124, FIG. 1) between the surface of the part and the first ply (114, FIG. 1). These two media, the resin and the reinforcing ply, have very different refractive indices and strong interference occurs at the interface between these two media. This particular property is exploited to detect the presence of a resin flash.

Figure 4:
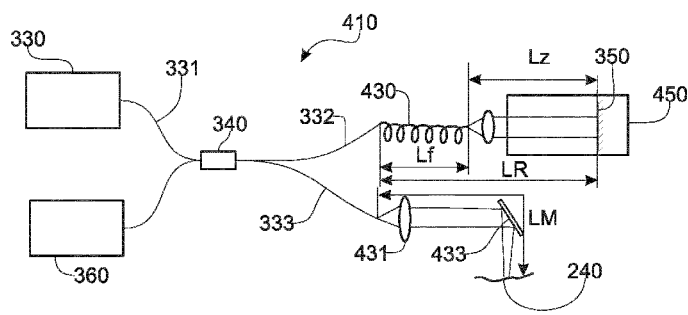
FIG. 4 schematically illustrates an improvement to the measurement head in FIG. 3, according to one embodiment of the device of the disclosure.

In FIG. 4, according to one embodiment, the OCT module (410) integrated into the measurement head (210) of the device of the disclosure comprises an optical fiber (430) of optical length Lf, on the optical path forming the reference leg. This optical length depends on the refractive index of the optical fiber. The reference mirror (350) is mounted to be moved translationally on a mirror moving device (450) so that the distance, Lz, between an exit of the optical fiber (430) and the reference mirror may be controlled, the length LR of the reference leg being the sum LR=Lf+Lz. This particular embodiment allows the measurement head (210) to be distanced from the surface of the part (100) and the scanning of the surface to be, at least partially, carried out via a scanning mirror (433). Thus, a first scan may be carried out rapidly, thereby decreasing the risk of collision between the part (100) and the manipulator (200) or the measurement head (210), thus making it simpler to program the movements, but this device also allows difficultly accessible zones (240) to be tested to be reached.

The optical path corresponding to the measurement leg, of length LM, comprises a scanning mirror (433) configured to project a measurement spot of controlled shape and size onto the zone (240) to be tested. For this purpose, the optical path comprises a focusing lens (431) allowing an optical spot smaller than a given diameter to be obtained. The diameter, D, of the focusing lens (431) depends on the diameter, D', of the optical spot targeted on the surface of the part, on the focal distance, f, and on the wavelength $\lambda$ of the laser radiation used, as defined by the relationship $D'=4\lambda f/\pi D$. By increasing the diameter of the lens transverse resolution is increased but depth of field is decreased. These parameters allow the dimensions of the strip from which the photons that will interfere originate to be defined. The image of the amplitude of the interference signal corresponds to the image of this strip, acting as a cross section, hence the expression tomographic image. In the embodiment using a scanning mirror (433) placed a large distance from the part, the distance LM is very similar to the distance between the scanning mirror (433) and the surface of the part (240).

The optical interferometry principle used for the OCT requires the lengths LM and LR to remain equal to within a tolerance that depends on the targeted application. Thus, the mirror moving device (450) of the reference mirror (350) allows, on the one hand, the length LR of the reference leg to be matched to length variations in the measurement leg due to the shape of the part. This compensation is achieved by varying the length Lz over a range that depends on the type of the tested parts, for example Lz=±250 mm for the testing of large aerospace parts.

On the other hand, the reference mirror (350) of the OCT system is moved over a small range of a few mm to measure the resin thickness. Thus, the mirror moving device (450) may comprise two actuators, each respectively ensuring the movement in one of the two ranges of variation of Lz. Thus, the length of the reference leg may be modified to be equivalent to the length of the measurement leg without having the measurement head dimensions modified within the same proportions as the modification of the length of the variation leg.

Figure 5:
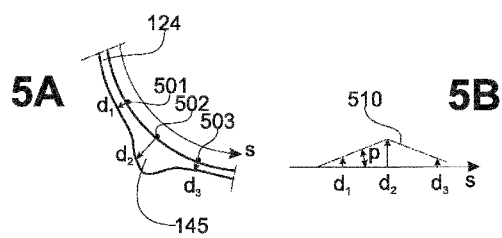
FIG. 5 illustrates in cross section, FIG. 5A, a schematic example of a series of thickness measurements in and around a resin flash, and shows, FIG. 5B, the amount of variation in these thickness measurements, this amount being used to detect the resin flash.

Referring for example to FIG. 5A, according to one embodiment, a first series of measurements ($d_1$, $d_2$, $d_3$) of the resin thickness of the first resin layer (124) is obtained with a coarse pitch along a curvilinear abscissa (s) transversely to the zone (240) to be tested, at some set measurement points (such as 501, 502, 503). In FIG. 5B, the variation in these resin thicknesses along this curvilinear abscissa (s), which corresponds to the scan direction, results in a resin thickness variation profile (510). According to one embodiment, the slope (p) of this resin thickness variation profile (510) is a criterion allowing the presence of a resin flash to be detected. Thus, from a series of measurements ($d_1$, $d_2$, $d_3$) carried out along the zone (240) to be tested, a probability of a presence of a resin flash may be estimated automatically by analyzing variations in the thickness of resin in the first layer (124). This probability may be estimated by comparison with standard signatures (standard resin thickness variation profiles and/or their slope) contained, for example, in a database stored in the information-processor device, or by training the device, especially by artificial intelligence techniques such as neural networks.

When the probability of a resin flash presence is significant (according to the result of the previous comparison), the measurement pitch of the measurement points and the precision of the resin thickness may be refined, in order to better fit the resin thickness variation profile (510) to the type or intensity of the pleats or corrugations that give rise thereto. Thus, a series of quick resin thickness measurements may be obtained by scanning with a measurement head comprising an OCT module (410, FIG. 4), configured to make measurements at a relatively large distance from the surface, for example LM=300 mm. Next, in zones of the part (100) in which the probability of a resin flash presence is detected as being significant, a series of accurate measurements may be carried out with a measurement head whose the OCT module (310, FIG. 3) is configured to make measurements at a smaller LM distance, for example between 10 mm and 30 mm, in order to characterize the resin flash (145) using these more accurate thickness measurements. This series of accurate measurements can be carried out with a finer measurement pitch. For this purpose, the manipulator (200) is configured such that the OCT measurement head advantageously can be changed.

Figure 6:
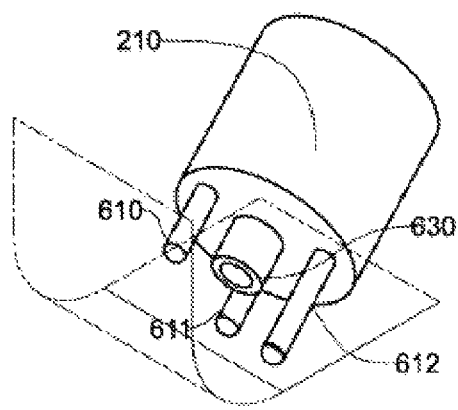
FIG. 6 is a perspective view of one embodiment of an OCT measurement head suitable for precisely measuring the resin thickness in a resin flash.

Referring for example to FIG. 6, the measurement head (210), according to one embodiment, is configured such that it comprises structure such as 610, 611, 612), for example taking the form of extendable feet whose length can be controlled, for example by digitally controlled actuators. These feet, when borne against the surface of the part, allow an objective (630) comprising the focusing lens of the laser beam forming the measurement leg to be positioned, thus allowing the measurement of the resin thickness to be carried out with a higher precision. Alternatively or in addition, the objective (630) may be positioned relative to the surface of the part (100) by contactless measurement structure(s) (not shown).

Figure 7:
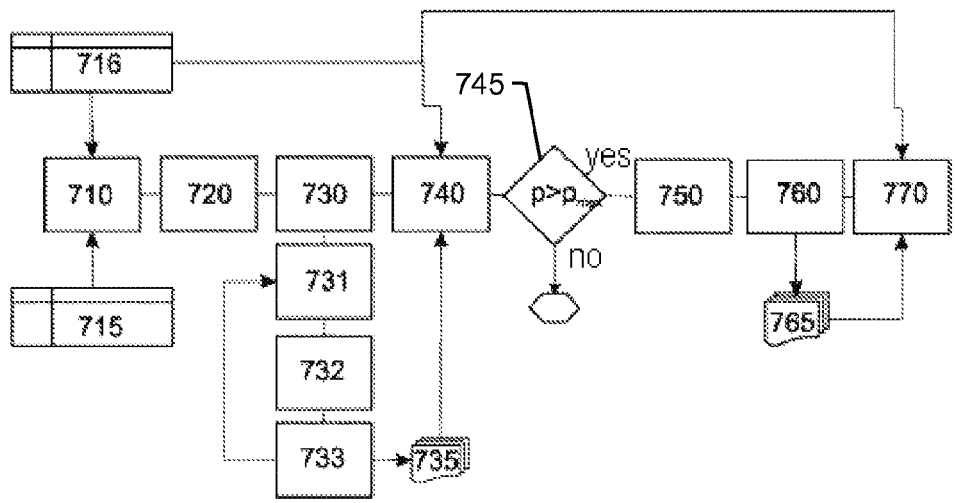
FIG. 7 is a flowchart of the method of the disclosure.

Referring for example to FIG. 7, according to one embodiment, the method of the disclosure comprises an initialization step (710), carried out by information-processor (250), comprising acquiring and recording a geometric definition (715) of the part (100) to be tested. This geometric definition (715) may originate from a CAD/CAM definition of the part to be tested, in formats known in the art. According to one embodiment, the initialization step (710) also comprises acquiring a file (716), called a criteria file, that comprises, depending on the type of the part (100) to be tested, tolerance values relating to the resin thickness variation profile (510). From the criteria file (716) and the geometric definition (715) of the part (100) to be tested, a program of movement of the manipulator (200) for the next measurement steps on the part (100) to be tested is generated in a programming step (720). This programming step may be carried out automatically or by a programmer. The movement program thus generated is sent to the manipulator (200). In an acquisition step (730), the manipulator (200) moves to some measurement points, according to the movement program, and measures resin thickness down to the first ply (114) in the zones to be tested. These measurements comprise illuminating (731) each measurement point with the OCT source, and, for each measurement point, in determining (732) the resin thickness down to the first ply (114), at this measurement point, using an Optical Coherence Tomography approach as described previously, and finally in recording (733) the thickness measured at this measurement point, with the spatial coordinates of the measurement point, in an acquisition file (735). In a processing step (740), the resin thickness variation profile (510) thus produced is compared with the criteria file (716). By way of example, the value of the slope (p) of the resin thickness variation profile is compared (745) with the slope tolerance value recorded in the criteria file (716). In the case where this slope is lower than a maximum allowable slope value ($p_{max}$) then the part is declared to be in specification. In the case where the value of the slope (p) is higher than the maximum allowable slope value ($p_{max}$), and according to one embodiment of the method of the disclosure, the OCT measurement head is changed in a reconfiguration step (750). A new acquisition cycle (760), comprising at least steps 731, 732, 733, 730 and 740, is begun with the new OCT measurement head, the resin thickness measured at the measurement points being recorded in an acquisition file (765). This acquisition file (765) is then compared (770) with the criteria file (716), as described above, in order to characterize the resin flash.

The above description and the embodiments demonstrate that the disclosure achieves the intended objectives. In particular, it allows a resin flash to be automatically detected in a composite part and this resin flash to be characterized with a view to detecting the presence of an out of tolerance pleat or corrugation in the reinforcing fibers.

While the disclosure herein has been described herein in reference to specific embodiments, features, and illustrative embodiments, it will be appreciated that the utility of the subject matter is not thus limited, but rather extends to and encompasses numerous other variations, modifications and alternative embodiments, as will suggest themselves to those of ordinary skill in the field of the present subject matter, based on the disclosure herein. Various combinations and sub-combinations of the structures and features described herein are contemplated and will be apparent to a skilled person having knowledge of this disclosure. Any of the various features and elements as disclosed herein may be combined with one or more other disclosed features and elements unless indicated to the contrary herein. Correspondingly, the subject matter as hereinafter claimed is intended to be broadly construed and interpreted, as including all such variations, modifications and alternative embodiments, within its scope and including equivalents of the claims. It is understood that various details of the presently disclosed subject matter may be changed without departing from the scope of the presently disclosed subject matter. Furthermore, the foregoing description is for the purpose of illustration only, and not for the purpose of limitation.

The invention claimed is:

1. A method for automatically detecting and characterizing a resin flash on a surface of a composite part comprising a matrix formed from a transparent or scattering resin and a fibrous reinforcement, the method comprising:
   a) obtaining a geometric definition of a zone of a part to be tested;
   b) obtaining a file, referred to as a criteria file, comprising values of resin thickness tolerances corresponding to the zone to be tested;
   c) illuminating a portion, referred to as a measurement point, of the surface of the zone to be tested using a laser source having a low temporal coherence;
   d) measuring a resin thickness at the measuring point using an optical coherence tomography approach;
   e) recording the resin thickness measured in step d) and spatial coordinates of the measurement point;
   f) moving the laser source to another measurement point and repeating steps c) to f) so as to carry out a scan until the zone to be tested has been entirely covered; and
   g) comparing a resin thickness variation profile of the zone to be tested with the criteria file.

2. The method according to claim 1, comprising, before step g):
   calculating a slope of resin thickness variation profile in one of the scan directions.

3. The method according to claim 1, comprising carrying out steps c) to g) with an OCT measurement head comprising a first OCT module and in that, if the presence of a resin flash is detected in step g), comprising:
   j) changing the OCT measurement head;
   k) carrying out steps c) to g) with changed OCT measurement head comprising an OCT measurement module configured to improve a detection precision of the resin flash.

4. A fully automatic device for automatically detecting and characterizing a resin flash on a surface of a composite part comprising a matrix formed from a transparent or scattering resin and a fibrous reinforcement, the fully automatic device comprising:

i) an OCT measurement head comprising an OCT measurement module;
ii) a manipulator configured to move the OCT measurement head in space; and
iii) an information-processor comprising a controller configured to pilot the manipulator and memory for acquiring a definition of geometry of a zone to be tested, for recording measurements in an acquisition file, for storing a criteria file, and for carrying out calculations relating to the comparison of the acquisition file with the criteria file; and
wherein the fully automatic device is configured, by virtue of instructions stored in the memory and executable by the controller, to execute the instructions using the controller and to:
a) obtain a geometric definition of the zone of a part to be tested;
b) obtain the criteria file comprising values of resin thickness tolerances corresponding to the zone to be tested;
c) illuminate a portion, referred to as a measurement point, of the surface of the zone to be tested using a laser source having a low temporal coherence;
d) measure a resin thickness at the measuring point using an optical coherence tomography approach;
e) record the resin thickness measured in step d) and spatial coordinates of the measurement point;
f) move the laser source to another measurement point and repeat steps c) to f) so as to carry out a scan until the zone to be tested has been entirely covered; and
g) compare a resin thickness variation profile of the zone to be tested with the criteria file.

5. The device according to claim 4, further comprising:
v) an optical path, referred to as a measurement leg, of length LM, comprising a scanning mirror configured to project onto a surface of the part a laser radiation from a low temporal coherence source; and
vi) an optical path, referred to as a reference leg, separate from the optical path of the measurement leg, and comprising an optical fiber of length Lf and a reference mirror placed at a distance Lz from an exit of the optical fiber such that LM=Lf+Lz.

6. The device according to claim 5, comprising:
vii) structure for changing an active OCT measurement head; and
viii) a second OCT measurement head comprising structure configured to adjust focal distance of a low coherence laser beam relative to a surface of the part.

* * * * *